United States Patent [19]
Bank et al.

[11] Patent Number: 5,567,834
[45] Date of Patent: Oct. 22, 1996

[54] PROCESS FOR PREPARATION OF β-ALKENYLTRIMETHYLSILANES

[75] Inventors: Howard M. Bank, Freeland; Binh T. Nguyen, Midland, both of Mich.

[73] Assignee: Dow Corning Corporation, Midland, Mich.

[21] Appl. No.: 594,963

[22] Filed: Jan. 31, 1996

[51] Int. Cl.$^6$ ........................................... C07F 7/08
[52] U.S. Cl. ................................. 556/442; 556/468
[58] Field of Search ........................... 556/442, 468

[56] References Cited

U.S. PATENT DOCUMENTS

| | | | |
|---|---|---|---|
| 2,787,627 | 4/1957 | Kuriyagawa et al. | 556/468 |
| 4,604,477 | 8/1986 | Rich | 556/468 X |
| 5,187,291 | 2/1993 | Seiler et al. | 556/442 |

OTHER PUBLICATIONS

Urata et al., Bull, Chem. Soc. Jpn. 57:607–608 (1984).

*Primary Examiner*—Paul F. Shaver
*Attorney, Agent, or Firm*—William F. Boley

[57] ABSTRACT

A process for making β-alkenyltrimethylsilanes and trimethylsilyl carboxylates. The process comprises contacting a mixture comprising hexamethyldisilane and an alkene carboxylate having a β-unsaturated carbon atom with novel organo-palladium and organo-nickel complexes, as catalysts, at a temperature within a range of about 100° C. to 250° C. The present process is especially useful for making allyltrimethylsilane and trimethylsilyl acetate.

17 Claims, No Drawings

PROCESS FOR PREPARATION OF β-ALKENYLTRIMETHYLSILANES

BACKGROUND OF INVENTION

The present invention is a process for making β-alkenyltrimethylsilanes and trimethylsilyl carboxylates. The process comprises contacting a mixture comprising hexamethyldisilane and an alkene carboxylate having a β-unsaturated carbon atom with novel organo-palladium and organo-nickel complexes as catalysts at a temperature within a range of about 100° C. to 250° C. The present process is especially useful for making allyltrimethylsilane and trimethylsilyl acetate.

β-Alkenyltrimethylsilanes and trimethylsilyl carboxylates are useful intermediates for introducing organofunctional silicon functionalities into silicone and organic polymers. The present method provides a method for converting hexamethyldisilane to these intermediates in near quantitative yield.

Urata et al., Bull. Chem. Soc. Jpn. 57:607–608 (1984) teach that allylic esters can react with hexamethyldisilane in the present of catalytic amounts of $Pd(PPh_3)_4$, $Pd\{P(OPh)_3\}_4$, or $RhCl(PPh_3)_3$ (Ph=phenyl) to give the corresponding allylic silanes in good yield. Urata et al. reported that $P_2\{P(OPh)_3\}_4$ effectively catalyzed the reaction of allyl acetate with hexamethyldisilane to give an excellent yield of β-alkenyltrimethylsiloxane. However Pd $(PPh_3)_4$ and RhCl $(PPh_3)_3$ caused significant formation of propylene and (E)-1-propenyltrimethylsilane resulting from the double-bond migration of allyltrimethylsilane.

The present inventors have discovered novel organo-palladium and organo-nickel complexes which can serve as catalysts to effect the reaction between hexamethyldisilane and alkene acetates to form β-alkenyltrimethylsilanes and trimethylsilyl carboxylates, without the double-bond shift as described in Urata et al., supra.

SUMMARY OF INVENTION

The present invention is a process for making β-alkenyltrimethylsilanes and trimethylsilyl carboxylates. The process comprises contacting a mixture comprising hexamethyldisilane and an alkene carboxylate having a β-unsaturated carbon atom with novel organo-palladium and organo-nickel complexes, as catalysts, at a temperature within a range of about 100° C. to 250° C. The present process is especially useful for making allyltrimethylsilane and trimethylsilyl acetate.

DESCRIPTION OF INVENTION

The present invention is a process for making β-alkenyltrimethylsilanes and trimethylsilyl carboxylates. The process comprises contacting a mixture comprising hexamethyldisilane and an alkene carboxylate described by formula $$R^1{}_2C=C(R^1)-CH_2-OC(O)R^2 \quad (1)$$

with a catalyst described by formula $$(R^3PPh)_2PdX_2 \text{ or} \quad (2)$$

$$(R^3{}_3P)_2NiX_2, \quad (3)$$

at a temperature within a range of about 100° C. to 250° C; where each $R^1$ is independently selected from a group consisting of hydrogen, saturated hydrocarbon radical comprising about 1 to 18 carbon atoms, aralkyls, and aryls; $R^2$ is selected from a group consisting of saturated hydrocarbon radicals comprising about 1 to 18 carbon atoms, aralkyls, and aryls; each $R^3$ is an independently selected alkyl comprising 1 to 8 carbon atoms; Ph is phenyl; and each X is an independently selected halogen atom selected from a group consisting of chlorine and bromine.

The present process can be conducted as a batch process, semi-continuous, or continuous process. The process can be conducted in standard type reactors suitable for retaining the feed materials under pressure.

The mixture of the present process comprises hexamethyldisilane. The hexamethyldisilane can be made by any standard method known in the art. The hexamethyldisilane can be a by-product of a process for making organohalosilanen where an organic halide is reacted with elemental silicon at an elevated temperature in the presence of a catalyst. The hexamethyldisilane can be part of a high-boiling mixture (>70° C.) resulting from the distillation of the product of a process where methyl chloride is reacted with elemental silicon at an elevated temperature in the presence of a catalyst to form monosilanes. The composition of such a high-boiling mixture which may be useful in the present process is described in Ferguson et al., U.S. Pat. No. 5,430,168, which is incorporated by reference for its teaching of such compositions.

The mixture of the present process further comprises an alkene carboxylate as described by formula (1). In formula (1), each $R^1$ is independently selected from a group consisting of hydrogen, saturated monovalent hydrocarbon radical comprising about 1 to 18 carbon atoms, aralkyls, and aryls. In addition to hydrogen atoms $R^1$ can be, for example, an alkyl such as methyl, ethyl, propyl, tert-butyl, decyl, and octadecyl; a cycloalkyl such as cyclopentyl and cyclohexyl; aralkyls such as benzyl, beta-phenylethyl, and beta-phenylpropyl; and aryls such as phenyl, tolyl, and naphthyl. Preferred is when $R^1$ is a hydrogen atom.

In formula (1), $R^2$ is selected from a group consisting of saturated monovalent hydrocarbon radicals comprising about 1 to 18 carbon atoms, aralkyls, and aryls. $R^2$ can be any of those hydrocarbon radicals as described for $R^1$. Preferred is when $R^2$ is a saturated monovalent hydrocarbon radical comprising about 1 to 6 carbon atoms. Most preferred is when $R^2$ is methyl. The preferred alkene carboxylate for use in the present process is allyl acetate.

The mole ratio of alkene carboxylate to hexamethyldisilane added to the present process can be within a range of about 0.1:1 to 10:1. It is preferred that the alkene carboxylate be added to the process in stoichiometric excess in relation to the amount of hexamethyldisilane added. Preferred is when the mole ratio of alkene carboxylate to hexamethyldisilane is within a range of about 1:1 to 3:1.

The mixture comprising the hexamethyldisilane and alkene carboxylate is contacted with a catalyst as described by formula (2) or formula (3). In formula (2) and (3) each substituent $R^3$ is an independently selected alkyl comprising about 1 to 8 carbon atoms. $R^3$ can be, for example, methyl, ethyl, propyl, tert-butyl, butyl, pentyl, and octyl. Preferred is when $R^3$ is methyl or ethyl. In formulas (2) and (3) each substituent X is a halogen independently elected from a group consisting of bromine and chlorine. Preferred is when X is chlorine. Preferred catalysts for use in the present process are described by formulas $(Me_2PPh)_2PdCl_2$ and $(Et_3P)_2NiCl_2$, where Me is methyl, Et is ethyl, and Ph is phenyl.

The concentration of catalyst added to the present process can be that providing about $1 \times 10^{-2}$ g.atom to $1 \times 10^{-5}$ g.atom of palladium or nickel per mole of alkene carboxylate. Preferred is when the catalysts provides about $5\times10^{-3}$ g.atom to $5\times10^{-4}$ g.atom of palladium or nickel per mole of alkene carboxylate.

In the present process, the mixture comprising the hexamethyldisilane and alkene carboxylate is contacted with the catalyst at a temperature within a range of about 100° C. to 250° C. A preferred temperature is within a range of about 150° C. to 225° C.

The products of the present process are β-alkenyltrimethylsilanes described by formula $Me_3Si-CH_2-(R^1)C=CR^1_2$ and trimethylsilyl carboxylates described by formula $Me_3Si-OC(O)R^2$, where Me is methyl and $R^1$ and $R^2$ are as previously described. A preferred product of the present process is β-allyltrimethylsilane.

The following examples are provided to illustrate the present invention. These examples are not intended to limit the scope of the claims herein.

The reactions reported in the examples were conducted in sealed pyrex glass tubes. A reaction mixture as described in each example was placed in the glass tube and cooled in an IPA dry ice bath. The tube was then heat sealed and heated at the temperature and for the time described for each example. At the end of the described reaction period the content of the tube was cooled and analyzed by gas chromatography using a flame ionization detector (GC-FID). The results are reported as the area percent (area %) under the GC-FID trace. In the formulas of the examples Me is methyl and Ph is phenyl.

EXAMPLE 1

The reaction mixture comprise 0.29 g (0.003 mol) of $Me_3SiSiMe_3$, 0.3 g (0.004 mol) of allyl acetate, and 0.0036 g of $(Me_2PPh)_2PdCl_2$. The mixture was heated at 150° C. for 21 hours, then cooled and analyzed by GC-FID. The analysis indicated the presence of no $Me_3SiSiMe_3$, 16.6 area % allyl acetate, 47.0 area % allylSiMe$_3$, and 34.0 area % $Me_3SiOC(O)CH_3$.

EXAMPLE 2

The process described in Example 1 was repeated in the absence of the $(Me_2PPh)_2PdCl_2$ catalyst. No reaction occurred.

EXAMPLE 3

The reaction mixture comprised 0.29 g of $Me_3SiSiMe_3$, 0.3 g of allyl acetate, and 0.004 g of $(Et_3P)_2NiCl_2$. The mixture was heated at 150° C. for 21 hours, then cooled and analyzed by GC-FID. The analysis indicated the presence of 37.7 area % $Me_3SiSiMe_3$, 31.6 area % allyl acetate, 15.2 area % allylSiMe$_3$, and 14.3 area % $Me_3SiOC(O)CH_3$.

EXAMPLE 4

The reaction mixture comprised 0.29 g of $Me_3SiSiMe_3$, 0.3 g of allyl acetate, and 0.004 g of $(Et_3P)_2NiCl_2$. The mixture was heated at 200° C. for 21 hours, then cooled and analyzed by GC-FID. The analysis indicated the presence of 10 area % $Me_3SiSiMe_3$, 1.4 area % allyl acetate, 32.0 area % allylSiMe$_3$, and 47.5 area % $Me_3SiOC(O)CH_3$.

EXAMPLE 5

The process described in Example 4 was repeated in the absence of the $Et_3P)_2NiCl_2$ catalyst. No reaction occurred.

We claim:
1. A process for making β-alkenyltrimethylsilanes and trimethylsilyl carboxylates, the process comprising contacting a mixture comprising hexamethyldisilane and an alkene carboxylate described by formula

$$R^1_2C=C(R^1)-CH_2-OC(O)R^2$$

with a catalyst described by formula $$(R^3PPh)_2PdX_2 \text{ or}$$

$$(R^3_3P)_2NiX_2,$$

at a temperature within a range of about 100° C. to 250° C.; where each $R^1$ is independently selected from a group consisting of hydrogen, saturated hydrocarbon radicals comprising about 1 to 18 carbon atoms, aralkyls, and aryls; $R^2$ is selected from a group consisting of saturated hydrocarbon radicals comprising about 1 to 18 carbon atoms, aralkyls, and aryls; each $R^3$ is an independently selected alkyl comprising about 1 to 8 carbon atoms; Ph is phenyl; and each X is an independently selected halogen atom selected from a group consisting of bromine and chlorine.

2. A process according to claim 1, where the mixture comprises hexamethyldisilane present in a high-boiling mixture resulting from the distillation of the product of a process where methyl chloride is reacted with elemental silicon to form monosilanes.

3. A process according to claim 1, where $R^1$ is a hydrogen atom.

4. A process according to claim 1, where $R^2$ methyl.

5. A process according to claim 1, where the alkene carboxylate is allyl acetate.

6. A process according to claim 1, where the mole ratio of alkene carboxylate to hexamethyldisilane in the mixture is within a range of about 0.1:1 to 10:1.

7. A process according to claim 1, where the mole ratio of alkene carboxylate to hexamethyldisilane in the mixture is within a range of about 1:1 to 0 3:1.

8. A process according to claim 1, where each $R^3$ is independently selected from a group consisting of methyl and ethyl.

9. A process according to claim 1, where X is chlorine.

10. A process according to claim 1, where the catalyst is selected from a group consisting of $(Me_2PPh)_2PdCl_2$ and $(Et_3P)_2NiCl_2$, where Me is methyl, Et is ethyl, and Ph is phenyl.

11. A process according to claim 1, where the mixture comprises about $1\times10^{-2}$ g.atom of $1\times10^{-5}$ g.atom of palladium per mole of alkene carboxylate.

12. A process according to claim 1, where the mixture comprises about $5\times10^{-3}$ g.atom to $5\times10^{-4}$ g.atom of palladium per mole of alkene carboxylate.

13. A process according to claim 1, where the mixture comprises about $1\times10^{-2}$ g.atom to $1\times10^{-5}$ g.atom of nickel per mole of alkene carboxylate.

14. A process according to claim 1, where the mixture comprises about $5\times10^{-3}$ g.atom to $5\times10^{-4}$ g.atom of nickel per mole of alkene carboxylate.

15. A process according to claim 1, where the temperature is within a range of about 150° C. to 225° C.

16. A process according to claim 1, where the alkene carboxylate is allyl acetate, the mole ratio of alkene carboxylate to hexamethyldisilane in the mixture is within a range of about 1:1 to 3:1, the catalyst is $(Me_2PPh)_2PdCl_2$, where Me is methyl and Ph is phenyl, the mixtures comprises about $5\times10^{-3}$ g.atom to $5\times10^{-4}$ g.atom of palladium per mole of alkene carboxylate, and the temperature is within a range of about 150° C. to 225° C.

17. A process according to claim 1, where the alkene carboxylate is allyl acetate, the mole ratio of alkene carboxylate to hexamethyldisilane in the mixture is within a range of about 1:1 to 3:1, the catalyst is $(Et_3P)_2NiCl_2$, where Et is ethyl and Ph is phenyl, the mixture comprises about $5\times10^{-3}$ g.atom to $5\times10^{-4}$ g.atom of nickel per mole of alkene carboxylate, and the temperature is within a range of about 150° C. to 225° C.

* * * * *